United States Patent [19]

Gautier et al.

[11] Patent Number: 4,666,513

[45] Date of Patent: May 19, 1987

[54] PROCESS FOR THE SELECTIVE EXTRACTION OF COPPER USING 4-ACYL-(3H)-PYRAZOL-3-ONES

[75] Inventors: Jean-Claude Gautier, Ablon sur Seine; Serge Lecolier, Janville sur Juine; Claude Soriaux, Mennecy; Sammy Chevalier, Paris, all of France

[73] Assignee: Societe Nationale des Poudres et Explosifs, Paris, France

[21] Appl. No.: 593,863

[22] Filed: Mar. 27, 1984

[30] Foreign Application Priority Data

Apr. 19, 1983 [FR] France ................. 83 06393

[51] Int. Cl.$^4$ ........................................... C22B 15/08
[52] U.S. Cl. ............................ 75/117; 75/101 BE; 423/24; 423/DIG. 14; 548/364; 548/367
[58] Field of Search ............. 75/117; 423/24

[56] References Cited

U.S. PATENT DOCUMENTS

| | | | |
|---|---|---|---|
| 4,065,455 | 12/1977 | Mattison | 75/117 |
| 4,197,391 | 4/1980 | Uejima et al. | 75/117 |
| 4,255,395 | 3/1981 | Gallacher et al. | 423/24 |

FOREIGN PATENT DOCUMENTS 452178  5/1978  U.S.S.R. ................. 548/378

OTHER PUBLICATIONS

Okafor, "Spectrochim Acta, Part A", 1981, vol. 37A, No. 11, pp. 939–944.
Irving and Williams, "Nature", vol. 162, pp. 746–747, 1948.
Jensen, "Acta Chem. Scand.", vol. 13, pp. 1668–1670, 1959.
Kirk-Othmer Encyclo. of Chemical Tech, 2nd, Edit., vol. 6, pp. 1–24, 1965.
Zolotov et al., Extraction of Metals By Acylpyrazolones, Chem. Abst. 89, 81023X, 1978.
Chemical Abstracts, vol. 89, No. 8, 21, Aug. 21, 1978, p. 209, No. 63102t, Columbus, Ohio, USA.
Chemical Abstracts, vol. 92, No. 16, Apr. 1980, p. 477, No. 136129f, Columbus, Ohio, USA.

Primary Examiner—John M. Ford
Assistant Examiner—Kurt G. Briscoe
Attorney, Agent, or Firm—Bucknam and Archer

[57] ABSTRACT

Liquid/liquid extraction process for copper from an aqueous sulphuric acid solution acting on the concentrated mineral or semi-finished product to be treated.

The extraction is carried out in an organic solvent containing in solution an extraction agent derived from 2-phenyl-4-acyl-(3H)-pyrazol-3-ones, with the phenyl group subsitituted or unsubstituted.

Application to the upgrading of minerals.

11 Claims, 4 Drawing Figures

PROCESS FOR THE SELECTIVE EXTRACTION OF COPPER USING 4-ACYL-(3H)-PYRAZOL-3-ONES

This invention concerns the selective extraction of copper.

More specifically the invention concerns the selective extraction of copper from concentrated ores or concentrates containing it, using a liquid/liquid extraction technique.

Over the last twenty years much research has been carried out on upgrading more and more impoverished ores (with approximately 1% copper), difficult to concentrate or too complex to be treated using the classical methods of pyrometallurgy.

The development of extraction agents (hereafter called extractants) for copper with high extractive power has made it possible to develop solvent extraction techniques.

Several families of organic extractants have been proposed in order to concentrate leaching solutions by liquid/liquid extraction. The best known of these are chelating agents of the hydroxyl oxime type, amongst which to be specially recommended are those put on the market by General Mills under the generic heading of the LIX series and those marketed by Shell under the designation SME 529 and by ICI under the designation ACORGA P 5000 or chelating agents of the hydroxyquinoline type such as those marketed by Ashland Chemical under the designations KELEX 100 and KELEX 120.

At present 15% of the world's production of copper, viz 1.2 million tons is obtained by hydrometallurgy with the help of these extraction agents. Extraction on an industrial scale is then mainly carried out from sulphuric acid solutions of the mineral by means of extractants dissolved in organic diluting agents such as aliphatic or aromatic hydrocarbons with a high flash point such as the kerosenes, the naphthas and similar compounds. Mention can be made of SOLVESSO 150 and ESCAID 100 manufactured by ESSO among the most used of the commercial products.

The disadvantages of extractants in current use are essentially the following:

(1) The extractants of the LIX series, in particular LIX 64N which is the most developed product of this series, have:
  (a) a low copper extractive power despite very good selectivity with respect to Ni and Co which makes it necessary to work with organic phase and aqueous phase volumes with a high ratio or with an extremely high concentration of extractant; in either case the result is that a higher investment has to be made than normal either for the extraction installation or for the extractant to be used, with still in the final analysis a result which is inadequate.
  (b) a slight concomittant extraction of iron which makes it necessary to treat again the aqueous reextraction solution before the electrolysis phase which is the classical phase for purifying the extracted metal.
  (c) the necessity of operating at temperatures below 40° C. since LIX 64N contains 1% LIX 63 which is unstable above this temperature.

(2) For other extractants with similar structure such as the product with the commercial name SME 529 and the products of the ACORGA series (see above):
  (a) although they give higher extraction coefficients than the products of the LIX series and have better extraction and reextraction kinetics they still make reextraction very difficult so that the residual level of copper in the aqueous phase is too high (see J. A. Tumilty, Advance in extractive metallurgy, 1977, p. 123).
  (b) it is therefore necessary to add quite significant amounts of a modifier (in practice 4-nonylphenol). However, the improvement in reextraction which is likely to result has a low coefficient of extraction.

(3) For extractants of the KELEX type, in particular KELEX 100, used for sulphide minerals which give solutions more concentrated in copper (of the order 30–50 g/l), 4-nonylphenol is added to prevent the formation of a third phase.

Work carried out in recent years on the extraction of nonferrous metals, essentially copper, in a sulphuric acid medium, has thus been mainly concerned with tests aimed at improving existing systems and overcoming in some way or other the known disadvantages of these systems. In this way additives to such systems have been tested aimed at:
  (a) either improving the performances of the main extractant from the point of view of extractive power, selectivity and extraction kinetics,
  (b) or preventing the formation of a precipitate at the interface or the formation of a third phase.

On the other hand patent No. DD-A-142.059 describes a process for recovering metals, more specifically lead, zinc and copper without selectivity by leaching complex minerals by means of a solution of extraction agents chosen from complexing agents of the polydentate type, dissolved in organic solvents such as dialkyldithiophosphoric acids, 4-acyl-pyrazolones or dithiocarbamates dissolved in chlorinated hydrocarbons, aliphatic or aromatic hydrocarbons, alcohols or ketones.

In this process the minerals are not first treated with alkaline or acidic solutions.

This is not a liquid/liquid extraction but an attack on the crushed mineral by an organic solution of a complexing agent and then after separation of the solid residue, extraction of the metals from the said organic solution by means of a solution of a dilute (2N) mineral acid. This process leads to a nonselective extraction and makes it necessary to have an additional treatment stage so that each of the metals extracted together can be obtained pure.

The aim of this invention is the selective extraction of copper with a high yield from concentrated minerals or concentrates containing it by a liquid/liquid extraction technique.

The problem put in this way is solved by a liquid/liquid extraction process involving first reacting the concentrated mineral or concentrate with an acidic leaching agent in an aqueous medium, preferably sulphuric acid, and according to which the copper is extracted from the reaction solution by a liquid/liquid extraction using at least one appropriate 2-phenyl-4-acyl-5-alkyl(or phenyl)-(3H)-pyrazol-3-one in organic solution, the phenyl groups being possibly substituted by alkyl groups.

The process conforming to the invention has proved unexpectedly capable of providing quite exceptional extraction selectivity with respect to iron and extraction yield of copper, better extractive power than that of classical techniques, greater ease of operation and lower cost in view of the possibility of avoiding or at least cutting down the addition of modifiers such as nonylphenol which was indispensable up till now.

It has been found according to the invention that these results as well as others which follow in this text are obtained thanks to a process which constitutes the primary object of this invention and according to which a liquid/liquid extraction is carried out on copper from an aqueous sulphuric acid solution acting on the concentrated ore or concentrate to be treated using at least one extraction agent of the type 2-phenyl-4-acyl-5-alkyl-(or phenyl)-(3H)-pyrazol-3-one in an organic solvent suitable for diluting and dissolving this extraction agent and as much as possible the complex which the latter forms with the copper to be extracted.

More specifically the useful extraction agent conforming to the invention corresponds to the formula:

This β-dicarbonyl compound can just as well exist in one of the two keto-enol forms:

where $R_1$ represents a phenyl group, possibly substituted by one or several alkyl groups containing 1–12 carbon atoms where $R_2$ represents a branched or straight-chain alkyl group containing 1–12 carbon atoms or a phenyl group possibly substituted by 1 or several alkyl groups each containing 1–12 carbon atoms where Z represents a straight-chain or branched, saturated or unsaturated aliphatic group containing 1–21 carbon atoms and where $R_3$ represents H, a (2-phenyl-5-alkyl-(3H)-pyrazolyl-3-one)-carbony-4 or a (2-phenyl-5-phenyl-(3H)-pyrazolyl-3-one)-carbonyl-4 thus forming a bis acylpyrazolone with the formula:

wherein the phenyl groups may or may not be substituted by alkyl groups.

According to an advantageous form of the invention $R_1$ represents the phenyl group and $R_2$ an alkyl group with 1–5 carbon atoms preferably the methyl group; according to another advantageous form of the invention, $R_1$ represents a phenyl group substituted by an alkyl group with 8–12 carbon atoms.

Finally Z preferably represents an alkylene group with 6–17 carbon atoms, more specifically ethyl-1-pentylene, undecylene or heptadecylene with $R_3$=H and a $—(CH_2)_4$-group when $R_3$ represents a pyrazolylcarbonyl as defined above.

For greater clarity it should be pointed out that here it has been decided to designate these products as being derivatives of 4-acyl-(3H)-pyrazol-3-ones, this practically conforming to the official nomenclature in force since 1972 whereas the nomenclature in use before this date assigned the designation 4-acyl-2-pyrazolin-5-ones to products of this type. It is obvious that these are the same products.

Some of the compounds are new.

Thus the object of the invention is also the new products falling within the framework of the above-mentioned formula, more specifically the following:

(a) 2-phenyl-4-(2-ethylhexanoyl)-5-methyl-(3H)-pyrazol-3-one (b) 2-phenyl-4-isononanoyl-5-methyl-(3H)-pyrazol-3-one (c) di-1,6-(2-phenyl-5-methyl-4-pyrazolyl-3-one)-hexan-1,6-dione (d) 2-phenyl-4-undecenoyl-5-methyl-(3H)-pyrazol-3-one (e) 2-phenyl-4-oleoyl-5-phenyl-(3H)-pyrazol-3-one (f) di-1,10-(2-phenyl-5-phenyl-4-pyrazolyl-3-one)-decan-1,10-dione.

These compounds may be prepared from known products by techniques known to those in the field such as the method described by Jensen in Acta Chemica Scandinavica, 13, 1668 (1959) according to which the acid chloride with formula H-Z-COCl in the case of the monopyrazolones or ClOCZCOCl in the case of the dipyrazolones is made to react with the heterocylic compound, unsubstituted at position 4 in the presence of calcium hydroxide.

According to the invention an organic solvent is used to dilute and dissolve the extraction agent and the complex which the latter forms with copper; it must be practically insoluble in water and not disturb the action of the extraction agent. This organic solvent should preferably have a high flash point.

Generally it is advisable that the organic solvent can dissolve approximately 20–750 g/l and preferably approximately 50–200 g/l of the extraction agent.

Efficient organic solvents are aliphatic or aromatic hydrocarbons with a high flash point such as the kerosines, naphthas and similar compounds.

Amongst these solvents, the products available on the market under the name SOLVESSO and distributed by ESSO are very strongly recommended, especially the product corresponding to the trade name SOLVESSO 150 which is an aromatic petroleum solvent.

The extraction process according to the invention is carried out by putting the organic solvent containing the extraction agent in contact with the aqueous solution of the leaching agent containing the copper and other metal entities resulting from the action on the mineral. The leaching agent is preferably sulphuric acid. The two phases, the aqueous phase and the organic phase, can be put in contact by extraction techniques well known to those working in this field (continuous or discontinuous extraction, use of mixer-settlers or extraction columns, etc . . . ; countercurrent techniques should be preferably used for circulating the fluids).

The ratio of the volumes of the aqueous and organic phases depends on the apparatus used, the concentration of the extraction agent in the organic phase and the composition of the aqueous phase to be treated. A $V_{aq}/V_{org}$ ratio lying between approximately 3/1 and 1/3 is desirable.

The temperature at which the phases are put into contact and are separated is not a key factor; it is simply related to the flash point of the solvent used; a temperature between 20° and 60° C. is advisable in practice.

It seems that with certain acylpyrazolones recommended by the invention the complex formed between the copper and the extraction agent may be precipitated after a certain lapse of time. It has been found, and this constitutes an alternative process according to the invention, that this precipitation can be delayed without however inhibiting the action of the agent by adding approximately 2–20% by volume and preferably 10% by volume of 4-nonylphenol or an equivalent to the solution of the extraction agent in the organic solvent.

The aqueous phase undergoing the process according to the invention may belong to two different types; in fact, depending on the nature of the minerals or mineral concentrates and specifically the nature of the copper minerals to be treated, a distinction is made between two types of sulphuric acid solutions for extracting copper using hydrometallurgy:

(a) sulphuric acid solutions formed from oxide minerals with a low concentration of copper (1–10 g/l) containing iron, cobalt and nickel with variable contents and with pH lying between 1 and 3;

(b) sulphuric acid solutions formed from sulphide minerals with a high concentration of copper (15–40 g/l) also containing high concentrations of iron, nickel and cobalt and with pH lying between 1 and 3.

The solutions would be less stable at higher pH values; the extraction coefficient would be lower at lower pH values.

The invention is illustrated more specifically below, referring to preferred forms of implementation and to non-exhaustive examples of application.

The extraction characteristics of the products recommended by the invention have been compared with those of products currently used in industry for the same purposes viz:

LIX 64N (which contains 1% LIX 63)

for aqueous sulphuric acid solutions with a low copper content (approximately 3 g/l);

KELEX 100 for aqueous sulphuric acid solutions with a high copper content formed from copper sulphide minerals.

The corresponding comparative extraction tests have been carried out on synthetic solutions representative of industrial compositions normally treated and shown below:

| Composition of the solutions | | | |
|---|---|---|---|
| representative of minerals with low Cu content = aqueous phase type A | | representative of sulphide minerals = aqueous phase type B | |
| $H_2SO_4$ | dilute | $H_2SO_4$ | dilute |
| Cu | 3 g/l | Cu | 23 g/l |
| Fe | 3 g/l | Fe | 6 g/l |
| | | Ni | 18 g/l |
| | | Co | 1 g/l |
| (amount of $H_2SO_4$ sufficient for pH = 1 and 2.5) | | (amount of $H_2SO_4$ sufficient for pH = 1 and 2) | |

Based on a preliminary study on the possible diluents satisfying the definition given above preference was given to the aromatic petroleum solvent marketed under the name SOLVESSO 150.

As an alternative, finding its use essentially in those cases where it is necessary to prevent the formation of a more or less significant precipitate in the organic phase (usually occurring after several hours, for example after 12–24 hours), it has been advantageous to also add approximately 2–20%, preferably approximately 10% nonylphenol by volume to the organic extraction phase.

The other tests which have been carried out are referred to hereafter by reference to the figures of drawings in the appendix, of these.

In the case of FIG. 3 the aqueous phase does not contain copper at the beginning.

In the case of FIG. 4 the initial concentration of copper in the aqueous phase is 30 g/l which simulates an aqueous phase at the output of the copper electrolysis circuit, recycled as an aqueous stripping solution, i.e.

used to reextract the copper contained in the organic phase. The copper-bearing organic phase contains, in the examples of FIG. 3, the extraction agent 2-phenyl-4-(2-ethylhexanoyl)-5-methyl-(3H)-pyrazol-3-one (curve 3), LIX 64N (curve 1) and 2-phenyl-4-lauroyl-5-methyl-(3H)-pyrazol-3-one (curve 2) and in the examples of FIG. 4 the extraction agent 2-phenyl-4-(2-ethylhexanoyl)-5-methyl-(3H)-pyrazol-3-one (curve 2) and LIX 64N (curve 1).

Figure 1:
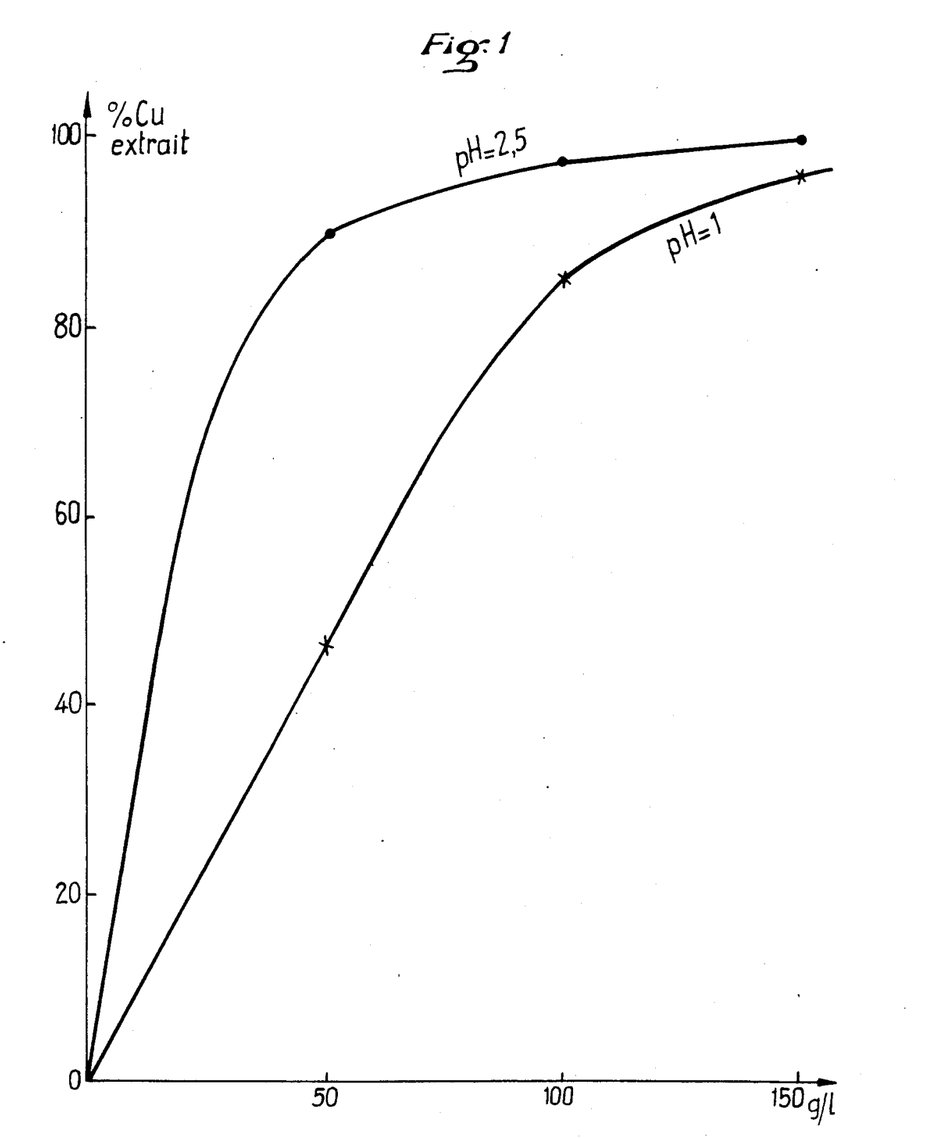
FIG. 1 represents the effect of the concentration of the extraction agent 2-phenyl-4-lauroyl-5-methyl-(3H)-pyrazol-3-one in SOLVESSO 150 plotted along the x-axis as well as that of the pH of the aqueous phase to be treated (aqueous phase type A) on the extraction (% Cu extracted plotted along the y-axis)
Figure 2:
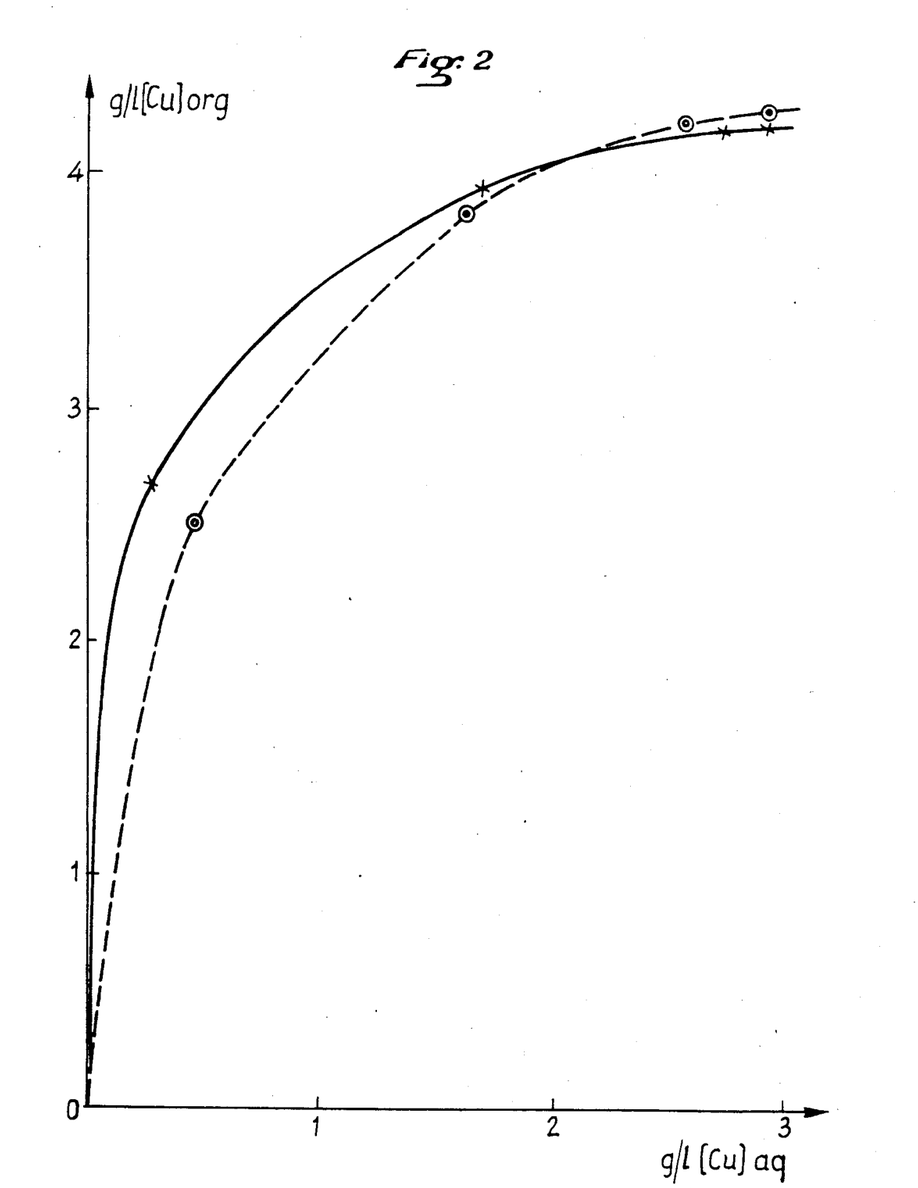
FIG. 2 represents the extraction isotherms obtained by treating an aqueous sulphuric acid solution type A at pH 2.5:
(1) For the dotted line curve, with the commercial product LIX 64N at a concentration of 15% in the diluent marketed under the name ESCAID 100;
(2) For the unbroken line curve, with 2-phenyl-4-lauroyl-5-methyl-(3H)-pyrazol-3-one at a concentration of 50 g/l in SOLVESSO 150+10 ml/100 ml volume of nonylphenol.

These tests whose results are given in the above-mentioned figures (to which it is worth referring) show that:

1. As far as the optimum concentration of the extraction agent and the pH of the aqueous phase best suited for obtaining maximum extraction are concerned:

in the case of a solution with low copper content:
- at pH 2.5 it is not necessary to use concentrations higher than 50 g/l in order to exhaust the aqueous phases with a limited number of stages,
- in comparison with the commercial extraction agent LIX 64N, the performance of 2-phenyl-4-lauroyl-5-methyl-(3H)-pyrazol-3-one dissolved in SOLVESSO (concentration 50 g/l) is equivalent to that of LIX 64N at a concentration of 136 g/l in the diluent ESCAID 100 (refer to table I and to the corresponding curves of FIG. 2).

in the case of an aqueous sulphuric acid solution with a high copper content compared to KELEX 100 at a concentration of 15% by volume (i.e. 143 g/l) in SOLVESSO 150 with the addition of 20% nonylphenol, the performance of the acrylpyrazolones (2-phenyl-4-lauroyl-5-methyl-(3H)-pyrazol-3-one and 2-phenyl-4-(2-ethylhexanonyl)-5-methyl-(3H)-pyrazol-3-one) is of the same order of magnitude at an equivalent concentration and even at a slightly lower concentration (i.e. 120–130 g/l).

Figure 3:
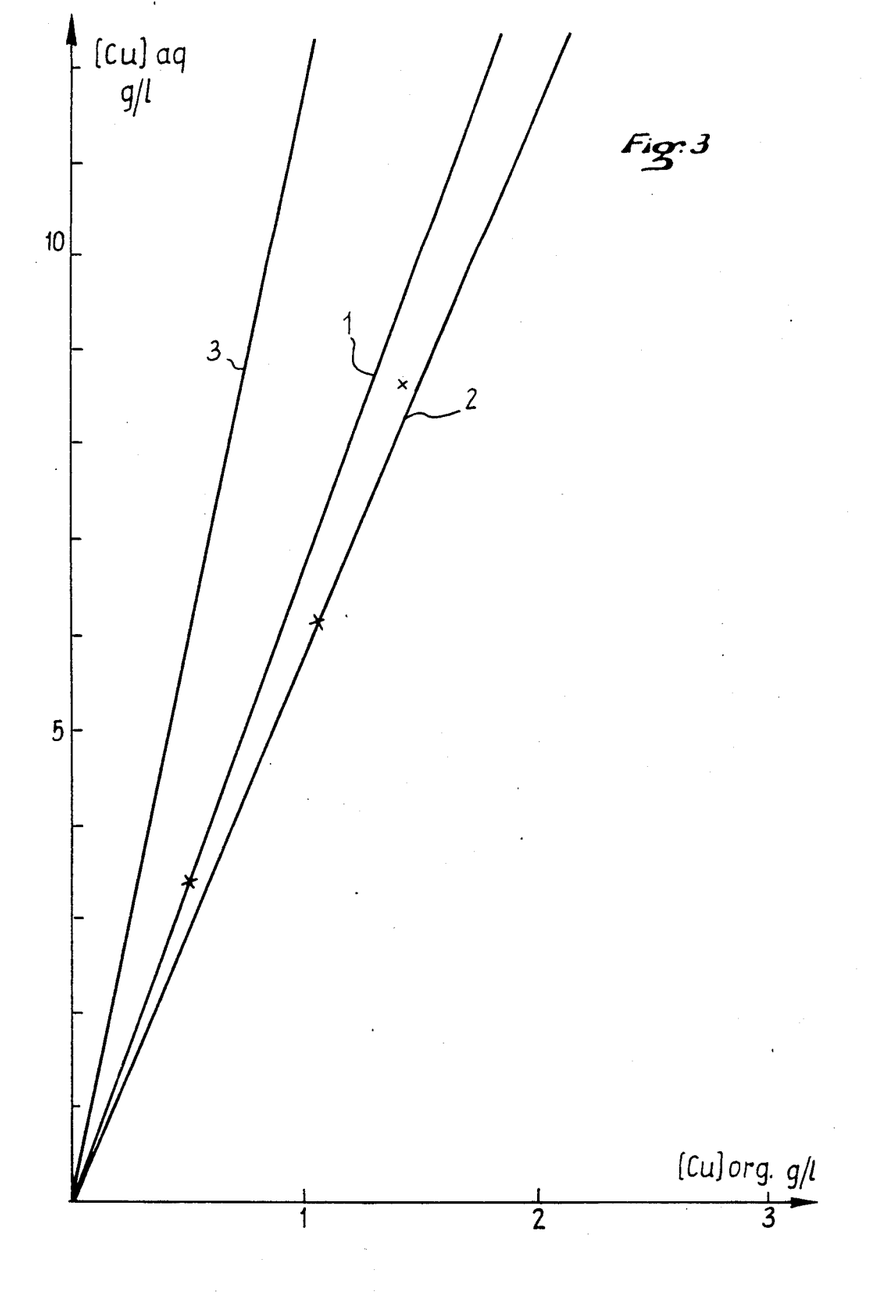
FIGS. 3 and 4 represent the reextraction isotherms obtained from successive contact between the same sulphuric acid aqueous phase and different organic phases containing copper.

(See table II and FIG. 3 curve 1 for LIX, curve 2 for lauroylpyrazolone and curve 3 for hexanoylpyrazolone).

2. The extraction isotherms plotted so that the saturation capacity of the extraction agent can be revealed (see FIG. 2) are practically indistinguishable for 2-phenyl-4-lauroyl-5-methyl-(3H)-pyrazol-3-one and LIX 64N which confirms the equivalent performance of "lauroylpyrazolone" at a concentration of only 50 g/l and LIX 64N with a concentration of 15% by volume, i.e. 136 g/l.

The tests which have been carried out make it possible to calculate the following extractive powers:

| extractant | mg of copper per g of extraction agent | relative efficacy of the pyrazolones and LIX 64 N |
|---|---|---|
| 4-lauroyl-P | 80 | 2.66 |
| 4-stearoyl-P | 70 | 2.33 |
| 4-(2-ethyl)hexanoyl-P | 90 | 2.83 |
| 4-nonanoyl-P | 104 | 3.46 |
| LIX 64 N | 30 | 1 |

P = 2-phenyl-5-methyl-(3H)—pyrazol-3-one

It can be concluded that for an equivalent amount, the 2-phenyl-4-acyl-5-methyl-(3H)-pyrazol-3-ones have an extractive power approximately 3 times higher than that of LIX 64N.

Figure 4:
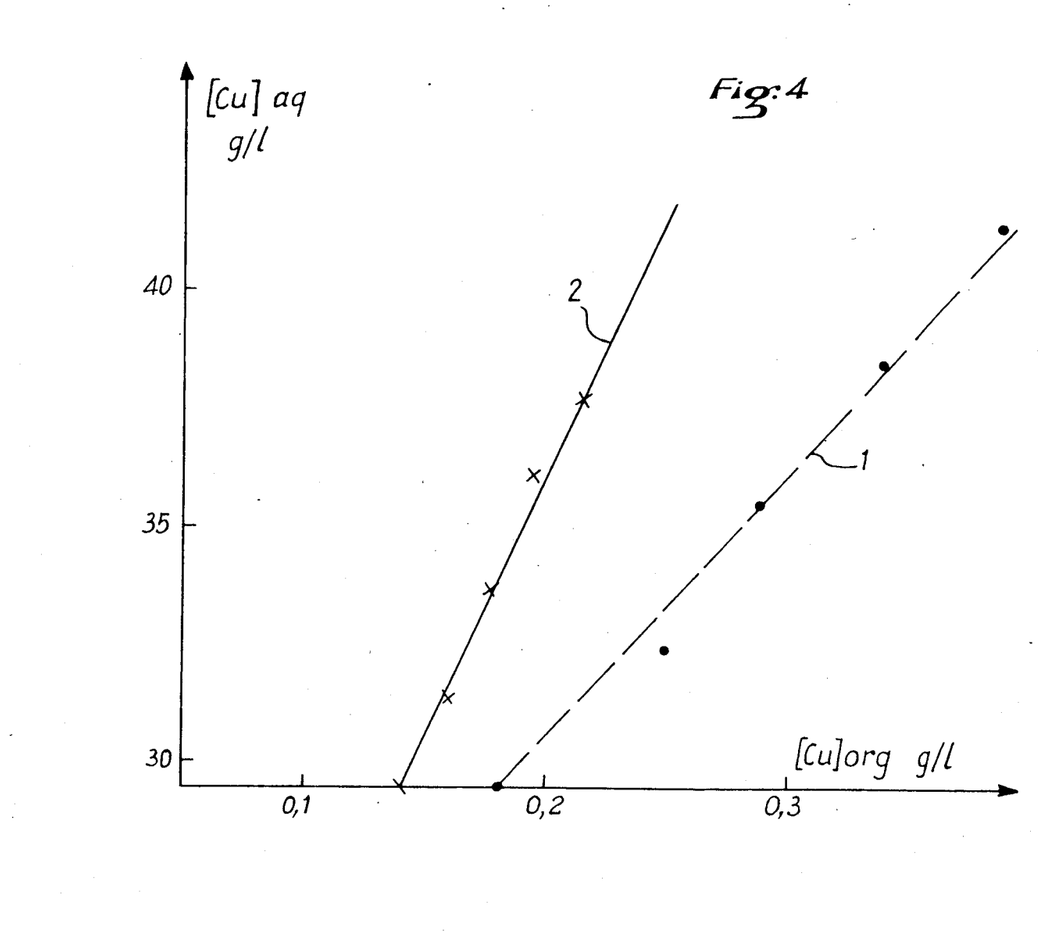

3. The isotherm reextraction curves obtained for the comparative reextraction tests with successive contact of the same aqueous sulphuric phase with different organic phases containing extractable metal entities are linear which proves that saturation of the aqueous phase has not been reached (FIGS. 3 and 4).

The isotherms for 2-phenyl-4-lauroyl-5-methyl-pyrazol-3-one and the product of the LIX type lie close to each other.

Reextraction is slightly easier in the case of 2-phenyl-4-(2-ethylhexanoyl)-5-methyl-(3H)-pyrazol-3-one. FIG. 4 shows particularly clearly in a representative case of industrial conditions (aqueous phase initially containing copper) that the reextraction of copper is more efficient in the case of 2-phenyl-4-(2-ethylhexanoyl)-5-methyl-(3H)-pyrazol-3-one than in the case of LIX 64N.

On the other hand, as far as the extraction selectivity is concerned, i.e. the separation of Cu and of the other metals Fe, Ni, Co the quantitative analysis made on the raffinate (exhausted aqueous phase) and on the organic phase (the results of which can be seen from tables I, II and IV below) has shown that the selectivity is better for a large majority of the products according to the invention than using the commercial products LIX 64N or KELEX 200 as extractants.

In particular table IV contains the results of calculating the Cu/Fe selectivity after 10 minutes of extraction. This selectivity is equal to the ratio of the partition coefficients:

$$\frac{K_{Cu}}{K_{Fe}} = \frac{[Cu]_{org}}{[Cu]_{aq}} : \frac{[Fe]_{org}}{[Fe]_{aq}}$$

where

[M]$_{org}$ represents the concentration of the metal M in the organic phase, and

[M]$_{aq}$ represents the concentration of the metal M in the aqueous phase.

Since the concentrations of iron and copper are initially the same another method of expressing the selectivity is to take the ratio [Cu]$_{org}$:[Fe]$_{org}$.

This selectivity is confirmed by the quantitative analysis results for iron and copper in aqueous solutions resulting from sulphuric acid reextraction (1N H$_2$SO$_4$) (table III below) and by the quantitative analysis results for the same elements in the corresponding organic phase.

In fact, in the presence of acylpyrazolone, 10 times less iron is extracted than in the presence of LIX 64N while the amounts of copper extracted are practically the same.

The selectivity with respect to nickel and cobalt is even better. In fact, these metals are not extracted by 2-phenyl-4-lauroyl-5-methyl-(3H)-pyrazol-3-one dissolved in SOLVESSO 150 (40 g/l) from an aqueous sulphuric acid solution in which they are present at a concentration of approximately 3 g/l.

This selectivity is again confirmed by the results of treating a sulphuric acid solution with a high copper content (23 g/l), also containing 6 g/l Fe, 18 g/l Ni and 1 g/l Co with 2-phenyl-4-(2-ethylhexanoyl)-5-methyl-(3H)-pyrazol-3-one in the diluent SOLVESSO 150 at a concentration of 0.42 moles per liter.

The bearing organic phase contained (see example 10 below):

Cu 8 g/l i.e. 34.8% extraction.
Ni 0.15 g/l i.e. 0.8% extraction.
Co<0.001 g/l i.e. <0.1% extraction.
Fe 0.06 g/l i.e. <1% extraction.

Example 11 below concerns a comparison between 2-phenyl-4-lauroyl-5-methyl-(3H)-pyrazol-3-one and the commercial product called KELEX 100 and again shows the superior selection obtained in the extraction of Cu in the presence of iron, nickel and cobalt with pyrazolone according to the invention.

The invention is illustrated in detail in the following examples which do not limit it in any way.

EXAMPLE 1

Extraction of copper from low-concentration solutions thereof at pH 2.5 by 2-phenyl-4-lauroyl-5-methyl-(3H)-pyrazol-3-one An aqueous sulphuric acid solution at pH 2.5 containing 2.9 g/l copper ($Cu^{2+}$) and 3.2 g/l iron is put in contact with a solution of 2-phenyl-4-lauroyl-5-methyl-(3H)-pyrazol-3-one in SOLVESSO 150 at a concentration of 100 g/l without an additive of the nonylphenol type.

The extraction is carried out volume by volume in a separating funnel at 20° C. with mechanical shaking for ½ hour. The pH of the aqueous solution at equilibrium is then measured.

After decantation the contents of copper and iron in the residual aqueous phase (the so-called raffinate) are measured by atomic absorption. The contents of the metals in the organic phase are calculated by difference.

The results obtained are the following:
pH at equilibrium: 1.4
Cu extracted: 99.7% of the initial Cu
Fe extracted: approximately 3% of the initial Fe.

EXAMPLE 2

Extraction of copper from low-concentration solutions at pH=1 by 2-phenyl-4-lauroyl-5-methyl-(3H)-pyrazol-3-one An aqueous sulphuric acid solution with pH 1 containing 2.9 g/l copper ($Cu^{2+}$) and 3.2 g/l iron is put in contact, volume by volume, with a solution of 100 g/l 2-phenyl-4-lauroyl-5-methyl-(3H)-pyrazol-3-one in SOLVESSO 150 without adding nonylphenol.

The extraction and analysis are carried out as in example 1.

The results are as follows:
pH at equilibrium: 0.8
Cu extracted: 85.3% of the initial Cu
Fe extracted: approximately 0%.

EXAMPLE 3

Extraction of copper from a low-concentration solution with pH 2.5 by 2-phenyl-4-(2-ethylhexanoyl)-5-methyl-(3H)-pyrazol-3-one An aqueous sulphuric acid solution with pH 2.5 containing 3 g/l copper ($Cu^{2+}$) and 3.2 g/l iron is put in contact, volume by volume, with a solution of 42 g/l 2-phenyl-4-(2-ethylhexanoyl)-5-methyl-(3H)-pyrazol-3-one in SOLVESSO 150.

The extraction and analysis are carried out as in example 1.

The results are as follows:
pH at equilibrium: 1.5
Cu extracted: 82% of the initial Cu
Fe extracted: approximately 0%.

EXAMPLE 4

Extraction of copper from a low-concentration solution at pH=2.5 by 2-phenyl-4-stearoyl-5-methyl-(3H)-pyrazol-3-one An aqueous sulphuric acid solution at pH 2.5 containing 2.9 g/l copper ($Cu^{2+}$) and 3.2 g/l iron is put in contact, volume by volume, with a solution of 62 g/l 2-phenyl-4-stearoyl-5-methyl-(3H)-pyrazol-3-one in SOLVESSO 150 with 10 ml/100 ml nonylphenol.

The extraction and the analysis are carried out as in example No. 1.

The results are as follows:
pH at equilibrium: 1.7
Cu extracted: 89.6% of the initial Cu
Fe extracted: approximately 0%.

EXAMPLE 5

Extraction of copper from a low-concentration solution with pH 2.3 by 2,5-diphenyl-4-oleoyl-(3H)-pyrazol-3-one An aqueous sulphuric acid solution with pH 2.3 containing 3.2 g/l copper ($Cu^{2+}$) and 3.35 g/l iron is put in contact, volume by volume, with a solution of 50 g/l 2,5-diphenyl-4-oleoyl-(3H)-pyrazol-3-one in SOLVESSO 150.

The extraction is carried out as in example 1. The quantitative analysis is made by measuring the contents of copper and iron by atomic absorption in the aqueous and organic phases.

pH at equilibrium: 1.4
Cu extracted: 68% of the initial Cu
Fe extracted: 0.3% of the initial Fe.

EXAMPLE 6

Extraction of copper from a low-concentration solution at pH 2.3 by 2-phenyl-4-undecenoyl-5-methyl-(3H)-pyrazol-3-one An aqueous sulphuric acid solution with pH 2.3 containing 3.13 g/l copper ($Cu^{2+}$) and 3.21 g/l iron is put in contact, volume by volume, with a solution of 50 g/l 2-phenyl-4-undecenoyl-5-methyl-(3H)-pyrazol-3-one is SOLVESSO 150 with 10% volume by volume nonylphenol.

The extraction and analysis are made as in example No. 5.

pH at equilibrium: 1.4
Cu extracted: 68% of the initial Cu
Fe extracted: 1.4% of the initial Fe.

EXAMPLE 7

Extraction of copper from a low-concentration solution at pH 2.3 by 2-phenyl-4-lauroyl-5-(n-propyl)-(3H)-pyrazol-3-one An aqueous sulphuric acid solution with pH 2.3 containing 3.13 g/l copper ($Cu^{2+}$) and 3.21 g/l iron is put in contact, volume by volume, with a solution of 50 g/l 2-phenyl-4-lauroyl-5-(n-propyl)-(3H)-pyrazol-3-one in SOLVESSO with 10% volume by volume nonylphenol.

The extraction and analysis are carried out as in example 5.

pH at equilibrium: 1.45
Cu extracted: 66% of initial Cu
Fe extracted: 0.6% of initial Fe.

EXAMPLE 8

Extraction of copper from a low-concentration solution with pH 2.5 by 2,5-diphenyl-4-lauroyl-(3H)-pyrazol-3-one An aqueous sulphuric acid solution with pH 2.5 containing 3 g/l copper ($Cu^{2+}$) and 3 g/l iron is put in contact for ½ hour, volume by volume, with a 0.14 M solution (50.6 g/l) of 2,5-diphenyl-4-lauroyl-(3H)-pyrazol-3-one in SOLVESSO 150 with 10% nonylphenol volume by volume.

The extraction and the analysis are carried out as in example No. 5.

pH at equilibrium: 1.4
Cu extracted: 76% of the initial Cu
Fe extracted: 0.7% of the initial Fe.

EXAMPLE 9

Extraction of copper from a medium-concentration solution with pH 2.3 by 2-phenyl-4-(2-ethylhexanoyl)-5-methyl-(3H)-pyrazol-3-one An aqueous sulphuric acid solution with pH 2.3 containing 6.16 g/l copper ($Cu^{2+}$) and 1.24 g/l iron is put in contact for ½ hour, volume by volume, with a solution of 100 g/l 2-phenyl-4-(2-ethylhexanoyl)-5-methyl-(3H)-pyrazol-3-one in SOLVESSO 150 with 2% nonylphenol (volume by volume).

The extraction and the analysis are carried out as in example No. 5.

pH at equilibrium: 1.4
Cu extracted: 76% of the initial Cu
Fe extracted: 1.2% of the initial Fe.

EXAMPLE 10

Extraction of copper from a high-concentration solution with pH=2 by 2-phenyl-4-(2-ethylhexanoyl)-5-methyl-(3H)-pyrazol-3-one An aqueous sulphuric acid solution with pH 2 containing 23 g/l copper, 6 g/l iron, 18 g/l nickel and 1 g/l cobalt is put in contact with a solution of 126 g/l 2-phenyl-4-(2-ethylhexanoyl)-5-methyl-(3H)-pyrazol-3-one in SOLVESSO 150.

The extraction is carried out in a separating funnel with mechanical shaking for ½ hour. The elements are analysed by atomic absorption either in the residual aqueous phase (raffinate) or in a reextraction aqueous phase (1N $H_2SO_4$) in order to increase the measuring sensitivity.

The results are as follows:
Cu extracted: 34.8% of the initial Cu
Ni extracted: 0.8% of the initial Ni
Fe extracted: 1% of the initial Fe
Co extracted: 0.1% of the initial Co.

EXAMPLE 11

Extraction of copper from a high-concentration solution with pH 2 by 2-phenyl-4-lauroyl-5-methyl-(3H)-pyrazol-3-one An aqueous sulphuric acid solution with pH 2 containing 22.6 g/l copper, 6.1 g/l iron, 19.2 g/l nickel and 0.8 g/l cobalt is put in contact, volume by volume, at 20° C. with a solution of 150 g/l 2-phenyl-4-lauroyl-5-methyl-(3H)-pyrazol-3-one in SOLVESSO 150.

The extraction is carried out in a separating funnel with shaking for ½ hour. The elements are analysed by atomic absorption in the residual aqueous phase (raffinate) and the extraction rates evaluated by subtraction.

The results are as follows:
final pH at equilibrium: 0.9
Cu extracted: 54.9% of the initial Cu
Fe extracted: 2.1% of the initial Fe
Ni extracted: 1.6% of the initial Ni
Co extracted: 2.5% of the initial Co.

By way of comparison extraction of the same acid solution by 143 g/l KELEX 100 in SOLVESSO 150 (with 20 ml/100 ml nonylphenol) gives the following results:
final pH at equilibrium: 1.1
Cu extracted: 45.3% initial Cu
Fe extracted: 4.8% initial Fe
Ni extracted: 2.7% initial Ni
Co extracted: 3.7% initial Co.

EXAMPLE 12

Extractive power of 2-phenyl-4-acyl-5-methyl-(3H)-pyrazol-3-ones

The extraction isotherms are obtained by successive contact of the same organic phase with a new aqueous phase under the following conditions:

Aqueous phase: sulphuric acid solution with pH 2.5 containing 3 g/l copper and 3 g/l iron.

Initial organic phase consists of 50 g/l of the acyl pyrazolone dissolved in SOLVESSO 150 with 10 ml/100 ml nonylphenol (except for 2-phenyl-4-(2-ethylhexanoyl)-5-methyl-(3H)-pyrazol-3-one where nonylphenol is not added).

The extractions are carried out volume by volume at 20° C. in separating funnels with a contact of ½ hour with shaking in each case. The copper is analysed by atomic absorption in the residual aqueous phases (raffinate) and the copper concentration in the organic phases evaluated by subtraction.

The extractive power of the extractant at saturation is calculated from the extraction isotherms by dividing the maximum metal concentration (in g metal per liter) determined from the isotherm by the concentration of extractant which is assumed to be pure expressed in g/l.

2-phenyl-4-lauroyl-5-methyl-(3H)-pyrazol-3-one gives:
80 mg Cu/g extractant;
2-phenyl-4-stearoyl-5-methyl-(3H)-pyrazol-3-one gives:
70 mg Cu/g extractant;
2-phenyl-4-(2-ethylhexanoyl)-5-methyl-(3H)-pyrazol-3-one gives:
90 mg Cu/g extractant;
2-phenyl-4-isononanoyl-5-methyl-(3H)-pyrazol-3-one gives:
104 mg Cu/g.

By way of comparison the extractive power of LIX 64N at a concentration of 136 g/l in ESCAID 100 is 30 mg Cu/g extractant.

EXAMPLE 13

Reextraction in the case of 2-phenyl-4-lauroyl-5-methyl-(3H)-pyrazol-3-one

Reextraction has been carried out under the following conditions: reextraction isotherms were obtained by successive contact of the same aqueous $H_2SO_4$ phase (1N) with a new organic phase containing 50 g/l 2-phenyl-4-lauroyl-5-methyl-(3H)-pyrazol-3-one in SOLVESSO 150 containing 10 ml/100 ml nonylphenol and 4 g/l copper; equilibrium corresponding to the lowest concentrations is obtained by exhausting the organic phase resulting from the first contact with a fresh aqueous phase.

The contacts are made in separating funnels at 20° C. for ½ hour. The concentrations are determined by atomic absorption in the aqueous phases and organic phases at the same time (after dilution in ethanol in the latter case). The extraction isotherms are collected together in FIG. 3 where curve 1 refers to LIX 64N at a concentration of 136 g/l in ESCAID 100 and curve 2 refers to 2-phenyl-4-lauroyl-5-methyl-(3H)-pyrazol-3-one.

EXAMPLE 14

Reextraction in the case of 2-phenyl-4-(2-ethylhexanoyl)-5-methyl-(3H)-pyrazol-3-one The same procedure as that of example 13 was followed. The reextraction isotherm was obtained from results of successive contact (volume by volume) of the same aqueous phase (1N $H_2SO_4$) with a new organic phase containing the extractant at a concentration of 0.14 mole/l i.e. 42 g/l and copper at a concentration of 3.3 g/l in SOLVESSO 150 without any nonylphenol.

The contacts took place in a separating funnel while shaking for ½ hour at ambient temperature.

The copper and iron were analyzed by atomic absorption in the aqueous reextraction phases.

The plotted isotherm is linear and gives slightly higher values than those obtained with LIX 64N and 2-phenyl-4-lauroyl-5-methyl-(3H)-pyrazol-3-one (FIG. 3 curve 3).

EXAMPLE 15

Reextraction by an aqueous stripping solution with 30 g/l copper. Case of 2-phenyl-4-(2-ethylhexanoyl)-5-methyl-(3H)-pyrazol-3-one Reextraction was carried out under the following conditions: the reextraction isotherms are determined by successive contact of the same organic phase (3N $H_2SO_4$, 30 g/l Cu) with a new organic phase containing 50 g/l 2-phenyl-4-(2-ethylhexanoyl)-5-methyl-(3H)-pyrazol-3-one in SOLVESSO 150 containing 10 ml/100 ml nonylphenol and 3.5 g/l Cu.

The contacts take place in a separating funnel at 20° C. for ½ hour. The concentrations are determined by atomic absorption at the same time in the aqueous phases and organic phases (after dilution in ethanol for the latter cases). The extraction isotherms are collected together in FIG. 4 where curve 1 refers to LIX 64N (at a concentration of 15% in ESCAID 100) and curve 2 refers to 2-phenyl-4-(2-ethylhexanoyl)-5-methyl-(3H)-pyrazol-3-one.

EXAMPLE 16

Copper/iron selectivity

Copper/iron selectivity has been studied by analysing the iron in 1N $H_2SO_4$ reextraction solutions obtained as described in example 13, the initial aqueous solution having a low copper concentration at pH 2.5 with 3 g/l copper and 3 g/l iron.

The following results are obtained for the final solutions most enriched in copper:
2-phenyl-4-lauroyl-5-methyl-(3H)-pyrazol-3-one
  Cu: 11.9 g/l
  Fe: 0.032 g/l.
2 phenyl-4-(2-ethylhexanoyl)-5-methyl-(3H)-pyrazol-3-one
  Cu: 11.5 g/l
  Fe: <0.01 g/l.
LIX 64N
  Cu: 13.8 g/l
  Fe: 0.310 g/l.

EXAMPLE 17

Extraction of copper and iron by the 4-acyl-(3H)-pyrazol-3-ones

Comparative selectivity

All the 4-acyl-(3H)-pyrazol-3-ones have been studied using the same procedure:

The aqueous solution of copper sulphate with 3 g/l copper ($Cu^{2+}$) and iron sulphate with 3 g/l iron is adjusted to pH 2.5 by adding $H_2SO_4$ under potentiometric control.

50 ml of this solution are poured into a cell with temperature controlled at 25° C. and equipped with a magnetic stirrer. 50 ml of the organic extraction phase (0.14 moles 4-acyl-(3H)-pyrazol-3-one in SOLVESSO 150 with or without depending on the case 10% nonylphenol by volume) are slowly added to this solution avoiding any agitation.

Finally the magnetic stirrer is set to 750 rpm and started.

Intermediate samples are taken in the aqueous and organic phases at times of 3, 10 and 60 minutes in order to measure the amount of extracted iron and copper by atomic absorption.

The results are collected in table IV expressed as an extraction percentage with respect to the amount initially present in the aqueous solution.

EXAMPLE 18

Preparation of 2-phenyl-4-(2-ethylhexanoyl)-5-methyl-(3H)-pyrazol-3-one

A mixture of 1044 g (6 moles) of 2-phenyl-5-methyl-(3H)-pyrazol-3-one are stirred in 4 liters of dioxan and the temperature brought to 60° C. in order to completely dissolve the pyrazolone. 888 g (12 moles) of calcium hydroxide $Ca(OH)_2$ are then added and then for 45 minutes 876 g (5.4 moles) of 2-ethylhexanoyl chloride. The temperature of the mixture reaches 95° C. and the mixture is kept at this temperature under stirring for 2 hours.

After cooling the reaction mixture is poured into 8 liters HCl (2N). An organic layer separates and 2 liters of toluene are added in order to facilitate decantation; The organic phase is dried over magnesium sulphate and the solvent eliminated under reduced pressure.

The oily residue obtained from a yield of 77% is rectified in a vacuum distillation apparatus and using a thin film technique. The product distils at 162° C. under 0.1 Pa.

The yield of purified product is 61%.
Identification has been carried out
(1) by NMR (proton)

The NMR spectrum taken in $CDCl_3$ as solvent and TMS as reference exhibits the following peaks:
at 2.5 ppm: singlet corresponding to the $CH_3$ at position 5 on the pyrazole ring,
between 0.7 and 3.1 ppm: multiplets attributed to the alkyl residue,
between 7.2 and 8 ppm: multiplets of the aromatic ring,
at 14 ppm: singlet corresponding to the enol proton.

(2) by elementary analysis

|  | C | H | N |
|---|---|---|---|
| experimental values: | 71.97% | 8.39% | 9.32% |
| theoretical values: | 71.93% | 8.00% | 9.46% |

(3) refractive index $n_d^{20} = 1.5560$
(4) density at 20° C. = 1.0678.

EXAMPLE 19

Preparation of 2-phenyl-4-isononanoyl-5-methyl-(3H)-pyrazol-3-one

Following the procedure of example 18 with the same proportions replacing 2-ethylhexanoyl chloride by isononanoyl chloride, 2-phenyl-4-isononanoyl-5-methyl-(3H)-pyrazol-3-one is obtained with a yield of 75%. This compound distils at 165° C. under 0.1 Pa. The NMR spectrum recorded in CDCl₃ with TMS as reference exhibits the peaks:

0.9–1.4 ppm (m); 2.5 ppm (s); 2.6–2.8 ppm (m); 7.2–8.1 ppm (m); 13.5 ppm (s).

EXAMPLE 20

Preparation of di-1,6-(2-phenyl-5-methyl-4-pyrazolyl-3-one)-hexane-1,6-dione 0.225 moles (39.15 g) of 2-phenyl-5-methyl-pyrazol-3-one are dissolved in 250 cm³ dioxan. 0.4 moles (29.6 g) Ca(OH)₂ are added and then quickly 0.1 moles (18.3 g) adipoyl chloride ClCO(CH₂)₄COCl are added. The mixture is refluxed for ¾ hour.

The reaction mixture is poured into 1.2 liters 2N hydrochloric acid. The solid product which precipitates is separated and redissolved in methylene chloride. The organic solution is dried over magnesium sulphate and then evaporated. A solid product is obtained with melting point 203° C. whose mass spectrum shows a peak (M+1) at 459.

EXAMPLE 21.

Preparation of 2-phenyl-4-oleoyl-5-phenyl-(3H)-pyrazol-3-one 0.2 moles, i.e. 47.2 g 2-phenyl-5-phenyl-pyrazol-3-one are dissolved in 600 cm³ dioxan at 60° C. 0.4 moles (29.6 g) lime are added and then for 30 minutes, 0.2 moles oleoyl chloride. The temperature of the reaction mixture is raised to 95° C. and it is left under stirring for 2 hours.

The cooled mixture is poured into 1 liter hydrochloric acid (2N). An oil separates out and is redissolved by methylene chloride. This organic phase is dried and then the solvent removed under vacuum.

An oily product is recovered with a yield of 84.5%. Purification has been carried out by isolating the cobalt complex of the oleoylpyrazolone.

50 g of impure derivative, i.e. 0.1 moles are mixed in 100 cm³ methanol with 0.055 moles anhydrous cobalt acetate, i.e. 9.73 g. The mixture is refluxed for 30 minutes.

The cobalt salt of the oleoylpyrazolone precipitates in methanol. It is filtered and washed in water.

The salt is placed in methylene chloride and sulphuric acid (3N) is added while stirring so as to destroy the cobalt complex and liberate the oleoylpyrazolone which is then solubilised in methylene chloride.

This organic phase is separated, washed in water, dried and the solvent removed under reduced pressure.

The oil obtained corresponds to the pure oleoylpyrazolone, identified by NMR (triplet of ethylene protons between 5.2 and 5.5 ppm).

EXAMPLE 22

Preparation of 2-phenyl-4-undecenoyl-5-methyl-(3H)-pyrazol-3-one

Following the procedure of example 18 with the same proportions but replacing 2-ethylhexanoyl chloride by undecenoyl chloride, a solid derivative is obtained which after recrystallisation is hexane has a melting point of 40° C.

The following peaks are identified in the NMR spectrum using CDCl₃ as the solvent and TMS as reference:

1 singlet at 2.5 ppm corresponding to the methyl at position 5 on the pyrazole ring;

1 triplet between 2.6 and 2.9 ppm corresponding to the methylene protons in the α position to the carbonyl group;

1 doublet between 1.9 and 2.1 ppm attributed to the methylene protons in the α position to the double bond;

multiplets between 0.9 and 2.4 ppm corresponding to the remaining protons of the alkyl chain;

multiplets between 4.8 and 6.1 ppm attributed to the protons of the double bond;

multiplets between 7.1 and 8 ppm of the aromatic protons;

a 14.5 ppm singlet originating from the enol proton.

EXAMPLE 23

Preparation of the di-1,10-(2-phenol-5-phenyl-4-pyrazolyl-3-one)-decan-1,10-dione 0.2 moles i.e. 47.2 g of 2-phenyl-5-phenyl-pyrazol-3-one are dissolved in 600 cm³ dioxan at 60° C. 0.4 moles (29.6 g) lime Ca(OH)₂ are added and then for 30 minutes 0.09 moles (21.5 g) sebacoyl chloride. The temperature of the mixture reaches 95° C. and this temperature is kept there for 2 hours.

After cooling, the reaction mixture is poured into 1 liter hydrochloric acid (2N). The precipitated solid is redissolved in 200 cm³ methylene chloride.

The organic solution is washed twice with 200 cm³ H₂SO₄ (3N) and then with distilled water. It is then dried and the solvent removed under reduced pressure.

The solid product obtained with a yield of 49.3% has a melting point of 168° C. and has an NMR spectrum in agreement with the formula of the compound.

EXAMPLE 24.

Preparation of 2-phenyl-4-lauroyl-5-phenyl-(3H)-pyrazol-3-one

Following the procedure of example 18 with the same proportions but replacing 2-phenyl-5-methyl-(3H)-pyrazol-3-one by 2-phenyl-5-phenyl-(3H)-pyrazol-3-one (MW=136.3 g; mp=136° C.) and 2-ethylhexanoyl chloride by lauroyl chloride a solid product is obtained which after recrystallisation in hexane has a melting point of 69° C.

The product was identified by NMR.

The purity was checked by elementary analysis.

|     | Theory | Found |
| --- | --- | --- |
| C % | 77.51 | 76.4 |
| H % | 8.13 | 8.2 |
| N % | 6.7 | 6.75 |

EXAMPLE 25

Preparation of
2-phenyl-4-(lauroyl)-5-propyl-(3H)-pyrazol-3-one

Following the procedure of example 18 with the same proportions but replacing 2-phenyl-5-methyl-(3H)-pyrazol-3-one by 2-phenyl-5-propyl-(3H)-pyrazol-3-one (MW=202; mp=114°) and 2-ethylhexanoyl chloride by lauroyl chloride a solid product is obtained which after recrystallisation in hexane has a melting point of 61° C.

The NMR spectrum recorded in CDCl$_3$ with TMS as reference exhibits characteristic peaks for 2-phenyl-4-lauroyl-5-propyl-(3H)-pyrazol-3-one:

0.7–2.8 ppm (multiplets of the CH$_3$ and CH$_2$ groups)
7.2–8.1 ppm (multiplets of the aromatic protons)
14.5 ppm (singlet of the enol proton).

EXAMPLE 26

Affinity of the 4-acyl-(3H)-pyrazol-3-ones for the Fe$^{3+}$ cation

All the 4-acyl-(3H)-pyrazol-3-ones have been studied following the same procedure:

An aqueous solution of ferric sulphate Fe$_2$(SO$_4$)$_3$ with 7.5 g/l Fe$^{3+}$ is adjusted to pH 2 by adding H$_2$SO$_4$ if necessary under potentiometric control.

This aqueous phase is put in contact with a solution of 4-acyl-(3H)-pyrazol-3-one (0.2M in SOLVESSO 150 without nonylphenol additive) for 15 minutes while shaking in a separating funnel. The extraction is carried out volume by volume at ambient temperature.

The analysis is carried out by measuring the iron content by atomic absorption in the aqueous and organic phases.

The results are collected together in table V. It was found that the 4-acyl-(3H)-pyrazol-3-ones have a significant affinity for iron when R$_1$ is an aliphatic chain or when ZR$_3$ is aromatic. The corresponding 4-acyl-pyrazolones therefore do not allow selective extraction of copper with respect to iron.

EXAMPLE 27

Extraction of copper and iron by
2-phenyl-4-thenoyl-5-methyl-(3H)-pyrazol-3-one

The extraction is carried out as in example 17: a 0.14M solution of 2-phenyl-4-thenoyl-5-methyl-(3H)-pyrazol-3-one in SOLVESSO 150 without nonylphenol is put in contact with an aqueous sulphuric acid solution containing 3 g/l Cu$^{2+}$ and 3 g/l iron (pH 2.5).

After analysing the copper and iron in the 2 phases the following results are obtained after 3 minutes of extraction:

Cu extracted: 71%
Fe extracted: 7.9%
[Cu]$_{org}$: [Fe]$_{org}$≃9, i.e. a bad selectivity with respect to iron.

EXAMPLE 28

Extraction of copper and iron by
2-(n-lauryl)-4-lauroyl-5-methyl-(3H)-pyrazol-3-one The extraction is carried out as in example No. 17: a 0.14M solution of 2-(n-lauryl)-4-lauroyl-5-methyl-(3H)-pyrazol-3-one in SOLVESSO 150 without nonylphenol as additive is put in contact with a sulphuric acid aqueous phase with 3 g/l Cu$^{2+}$ and 3 g/l iron (pH 2.5).

After anlysing the copper and iron in the 2 phases by atomic absorption the results are the following after 60 minutes extraction:

Cu extracted: 48.8%
Fe extracted: 6.9%
[Cu]$_{org}$: [Fe]$_{org}$≃7, i.e. a bad selectivity with respect to iron.

EXAMPLE 29

Extraction of copper and iron by
2-phenyl-4-benzoyl-5-methyl-(3H)-pyrazol-3-one

An organic phase containing 0.14M 2-phenyl-4-benzoyl-5-methyl-(3H)-pyrazol-3-one in SOLVESSO 150 with 10% nonylphenol is shaken up in a separating funnel, volume by volume with an aqueous sulphuric acid phase at pH 2.5 containing 3 g/l copper Cu$^{2+}$ and 3 g/l iron. The shaking up takes ½ hour at ambient temperature.

A precipitate of the complex with copper appears immediately.

An analysis is made of the aqueous phases by atomic absorption. The results are as follows:

Cu extracted: 97%
Fe extracted: 40%
[Cu]$_{org}$: [Fe]$_{org}$≃2.5, i.e. practically no selectivity with respect to iron.

TABLE I

EFFECT OF EXTRACTANT CONCENTRATION AND OF THE pH OF THE AQUEOUS PHASE ON THE EXTRACTION OF COPPER AND IRON

| Initial aqueous phase type A (dilute H$_2$SO$_4$) | Extractant concentration ||||||||||||
| --- | --- | --- | --- | --- | --- | --- | --- | --- | --- | --- | --- | --- |
| | 2-phenyl-4-lauroyl-5-methyl-(3H)—pyrazol-3-one |||||||||| LIX 64 N ||
| | 50 g/l ||| 100 g/l ||| 150 g/l ||| 15% (V/V).136 g/l |||
| | final pH | % extracted Cu | Fe | final pH | % extracted Cu | Fe | final pH | % extracted Cu | Fe | final pH | % extracted Cu | Fe |
| Cu: 2,9 g/l Fe: 3,2 g pH: 1 | 0,8 | 46,5 | ∼0 | 0,8 | 85,3 | ∼0 | 0,8 | 95,9 | ∼6 | 0,8 | 43,5 | ∼0 |
| Cu: 2,9 g/l Fe: 3,2 g/l | 1,5 | 90,0 | ∼0 | 1,4 | 99,7 | ∼3 | 1,4 | 99,9 | ∼6 | 1,4 | 91,2 | ∼6 |

TABLE I-continued

EFFECT OF EXTRACTANT CONCENTRATION AND OF THE pH OF THE AQUEOUS PHASE ON THE EXTRACTION OF COPPER AND IRON

| Initial aqueous phase type A (dilute $H_2SO_4$) | Extractant concentration | | | | | | | | | | |
|---|---|---|---|---|---|---|---|---|---|---|---|
| | 2-phenyl-4-lauroyl-5-methyl-(3H)—pyrazol-3-one | | | | | | | | LIX 64 N | | |
| | 50 g/l | | | 100 g/l | | | 150 g/l | | | 15% (V/V).136 g/l | | |
| | final pH | % extracted | | final pH | % extracted | | final pH | % extracted | | final pH | % extracted | |
| | | Cu | Fe | | Cu | Fe | | Cu | Fe | | Cu | Fe |
| pH: 2,5 | | | | | | | | | | | | |

~ means approximately
The diluent used was:
SOLVESSO 150 for the pyrazolone
the product called ESCAID 100 for the extractant of type LIX.

TABLE II

Effect of the extractant concentration and pH of the aqueous phase on the extraction of copper and the impurities: Fe, Co, Ni.

| Initial aqueous phase type B (dilute $H_2SO_4$) | Extractant concentration | | | | | | | | | | | | | | | | | | | |
|---|---|---|---|---|---|---|---|---|---|---|---|---|---|---|---|---|---|---|---|---|
| | 2-phenyl-4-lauroyl-5-methyl-(3H)—pyrazol-3-one | | | | | | | | | | | | | | KELEX 100 | | | | | |
| | 50 g/l | | | | | 100 g/l | | | | | 150 g/l | | | | | 15% (V.V).143 g/l | | | | | |
| | final pH | % extracted | | | | final pH | % extracted | | | | final pH | % extracted | | | | final pH | % extracted | | | |
| | | Cu | Fe | Ni | CO | | Cu | Fe | Ni | CO | | Cu | Fe | Ni | CO | | Cu | Fe | Ni | CO |
| Cu: 22,6 g/l Fe: 6,1 g/l Ni: 19,2 g/l Co: 0,8 g/l pH 1 | 0,9 | 13,5 | 0 | 0 | 0 | 0,8 | 34,5 | 0 | 0 | 0 | 0,8 | 56,6 | 17,6 | 16,7 | 11 | 0,7 | 40,7 | 7,9 | 0 | 0 |
| same concentrations pH 2 | 1,5 | 18,2 | 0 | — | — | 1,1 | 34,1 | 0 | — | — | 0,9 | 54,9 | 2,1 | 1,6 | 2,5 | 1,1 | 45,3 | 4,8 | 2,7 | 3,7 |

SOLVESSO 150 was used as the diluent for pyrazolone and for KELEX 100.

TABLE III

| Selectivity | Concentration in aqueous reextraction solutions of 1 N $H_2SO_4$ | |
|---|---|---|
| | Cu (g/l) | Fe (g/l) |
| 4-lauroyl-P | 11,9 | 0,032 |
| 4-(2-ethylhexanoyl)-P | 11,5 | <0,010 |
| LIX 64 N | 13,8 | 0,310 |

P = 2-phenyl-5-methyl-(3H)—pyrazol-3-one.
Initial aqueous solution, type A: Cu 3 g/l
Fe 3 g/l and pH = 2.5

TABLE IV

Extraction of copper in the presence of iron by 4-acyl-(3H)—pyrazol-3-ones

| 4-acyl-(3H)—pyrazol-3-ones | | | Copper extracted after | | | Iron extracted after | | | Selectivity at 10 min. = $\frac{K_{Cu}}{K_{Fe}}$ | Selectivity at 10 min = $\frac{[Cu]_{org}}{[Fe]_{org}}$ |
|---|---|---|---|---|---|---|---|---|---|---|
| $-R_1$ | $-R_2$ | $-Z-R_3$ | 3 min | 10 min | 60 min | 3 min | 10 min | 60 min | | |
|  | $-CH_3$ | $-CH\begin{matrix}C_2H_5\\C_4H_9\end{matrix}$ | 69,4% | 75,3% | — | 0,2% | 0,3% | 1,7% | 1013 | 251 |
|  | $-CH_3$ | $-_nC_{11}H_{23}$ | 83% | 86,8% | 86,8% | 0,2% | 0,3% | 0,8% | 2185 | 289 |
|  | $-CH_3$ | $-_nC_{17}H_{35}*$ | 55% | 70% | 70% | 0,2% | 0,2% | — | 1160 | 350 |
|  |  | $-(CH_2)_7-CH=*$ $CH-(CH_2)_7-CH_3$ | 59,4% | 76,8% | 81,5% | 0,05% | 0,1% | 0,2% | 3300 | 768 |
|  |  | $-_nC_{11}H_{23}$ | 62,9% | 72,2% | 74,7% | 0,3% | 0,7% | 2% | 370 | 103 |
|  | $-_nC_3H_7$ | $-_nC_{11}H_{23}$ | 48,0% | 66% | — | 0,3% | 0,7% | — | 285 | 94 |

TABLE IV-continued

Extraction of copper in the presence of iron by 4-acyl-(3H)—pyrazol-3-ones

| −R₁ | 4-acyl-(3H)—pyrazol-3-ones −R₂ | −Z−R₃ | Copper extracted after 3 min | 10 min | 60 min | Iron extracted after 3 min | 10 min | 60 min | Selectivity at 10 min. = KCu/KFe | Selectivity at 10 min = [Cu]org/[Fe]org |
|---|---|---|---|---|---|---|---|---|---|---|
|  | −CH₃ | −$_n$C₁₁H₂₃* | 42,6% | 65,9% | 88,9% | 0,25% | 1,7% | 1,7% | 111 | 39 |
| LIX 64 N (ESCAID) | | | 78,5% | 83,5% | — | 1,25% | 1,72% | — | 290 | 48 |

*nonylphenol (10%)
Initial aqueous solution: 3 g/l Cu - 3 g/l Fe

TABLE V

Extraction of iron by itself
contact time: 15 minutes

| R₁ | R₂ | −Z−R₃ | Iron extracted mg organic phase | extraction % |
|---|---|---|---|---|
| —⌬ | −CH₃ | −$_n$C₁₁H₂₃ | 155 mg | 2% |
| −$_n$C₁₂H₂₅ | −CH₃ | −$_n$C₁₁H₂₃ | 648 mg | 8,6% |
| —⌬ | −C₃H₇ | −$_n$C₁₁H₂₃ | 174 mg | 2,3% |
| —⌬ | —⌬ | −$_n$C₁₁H₂₃ | 132 mg | 1,8% |
| —⌬ | −CH₃ | −CH(C₂H₅)(C₄H₉) | 121 mg | 1,6% |
| —⌬ | −CH₃ | −$_n$C₁₇H₃₅ | 207 mg | 2,7% |
| —⌬ | −CH₃ | −⌬−C(CH₃)₃ | 648 mg | 8,6% |
| —⌬ | −CH₃ | —⌬ | 2205 mg | 29,4% |

Initial aqueous solution:
- 7.5 g/l Fe
- pH 2

We claim:

1. A process for the selective extraction of copper of the liquid/liquid type from an aqueous sulfuric acid solution acting on an ore which contains copper and Fe(III) or from a solution of a concentrate which contains copper and Fe(III), which consists of extracting said aqueous solution with a solution in an organic solvent of a compound of formula A or its enol forms A₂ or A₃

(A)

(A₂)

(A₃)

wherein

R₁ is a phenyl unsubstituted or substituted by at least one alkyl containing 1–12 carbon atoms;

R₂ is branched or straight-chain alkyl containing 1–12 carbon atoms or phenyl unsubstituted or substituted by at least one alkyl containing 1–12 carbon atoms;

Z is a straight-chain or branched, saturated or unsaturated aliphatic group containing 6–17 carbon atoms;

R₃ is H, (2-phenyl-5-alkyl-(3H)-pyrazol-4-yl-3-one)carbonyl or (2-phenyl-5-phenyl-(3H)-pyrazol-4-yl-3-one)-carbonyl to form a bis acylpyrazolone, said phenyl groups being unsubstituted or substituted by alkyl, forming a complex between said compound and copper, and extracting again copper from said solution in said organic solvent.

2. The process according to claim 1 wherein said complex is soluble in said organic solvent.

3. The process according to claim 1 wherein said organic solvent is essentially insoluble in water and has a high flash point.

4. The process according to claim 3 wherein said organic solvent is a member selected from the group consisting of aliphatic and aromatic hydrocarbons with high flash point.

5. The process according to claim 1, wherein said compound of formula A, A₂, A₃ is in a concentration of 20–750 g/l in the solvent.

6. The process according to claim 1 wherein the solution in the organic solvent also contains from 2 to approximately 20 ml/100 ml nonylphenol.

7. The process according to claim 1 wherein said compound is a member selected from the group consisting of 2-phenyl-4-(2-ethylhexanoyl)-5-methyl-(3H)-pyrazol-3-one;
2-phenyl-4-isononanoyl-5-methyl-(3H)-pyrazol-3-one;
1,6-di(2-phenyl-5-methyl-4-pyrazolyl-3-one)-hexan-1,6-dione;
2-phenyl-4-undecenoyl-5-methyl-(3H)-pyrazol-3-one;
2-phenyl-4-oleoyl-5-phenyl-(3H)-pyrazol-3-one;
1,10-di(2-phenyl-5-phenyl-4-pyrazolyl-3-one)-decan-1,10-dione;
2-phenyl-4-lauroyl-5-methyl-(3H) pyrazol-3-one;
2-phenyl-4-stearoyl-5-methyl-(3H)-pyrazol-3-one;
2-phenyl-4-nonanoyl-5-methyl-(3H)-pyrazol-3-one;
2-phenyl-4-lauroyl-5-n-propyl-(3H)-pyrazol-3-one;
2,5-diphenyl-4-lauroyl-(3H)-pyrazol-3-one.

8. The process according to claim 1 wherein $R_1$ is phenyl and $R_2$ is alkyl of 1–5 carbon atoms.

9. The process according to claim 1 wherein $R_1$ is phenyl substituted by alkyl of 8–12 carbon atoms.

10. The process according to claim 1 wherein Z is 1-ethylpentylene, undecylene or heptadecylene and $R_3$=H or Z is —$(CH_2)_4$— when $R_3$ is a pyrazolylcarbonyl group.

11. The process according to claim 1 wherein copper is reextracted from said solution in said organic solvent by electrolysis in aqueous sulfuric acid solution.

* * * * *